(12) United States Patent
Nogueira et al.

(10) Patent No.: US 9,986,679 B2
(45) Date of Patent: Jun. 5, 2018

(54) ALGINATE COATING FOR SETT TREATMENT

(71) Applicant: FMC Corporation, Philadelphia, PA (US)

(72) Inventors: Alessandro Leal Nogueira, Agua Branca (BR); Yemel Mayo Ortega, Marlton, NJ (US); Ricardo Camara Werlang, Uberlandia (BR)

(73) Assignee: FMC Corporation, Philadelphia, PA (US)

( * ) Notice: Subject to any disclaimer, the term of this patent is extended or adjusted under 35 U.S.C. 154(b) by 19 days.

(21) Appl. No.: 15/032,767

(22) PCT Filed: Oct. 29, 2014

(86) PCT No.: PCT/US2014/062884
§ 371 (c)(1),
(2) Date: Apr. 28, 2016

(87) PCT Pub. No.: WO2015/066171
PCT Pub. Date: Jul. 5, 2015

(65) Prior Publication Data
US 2016/0249523 A1    Sep. 1, 2016

Related U.S. Application Data

(60) Provisional application No. 61/898,219, filed on Oct. 31, 2013.

(51) Int. Cl.
*A01C 1/06* (2006.01)
*A01N 25/02* (2006.01)
(Continued)

(52) U.S. Cl.
CPC ............... *A01C 1/06* (2013.01); *A01G 1/001* (2013.01); *A01N 25/02* (2013.01); *A01N 47/40* (2013.01);
(Continued)

(58) Field of Classification Search
CPC .... A01C 1/00; A01C 1/06; A01C 1/08; A01G 1/001; A01N 25/02; A01N 47/40;
(Continued)

(56) References Cited

U.S. PATENT DOCUMENTS 5,706,602 A * 1/1998 Kohno .................... A01C 1/06
                                                                   47/57.6
5,977,023 A    11/1999 Inoue et al.
(Continued)

FOREIGN PATENT DOCUMENTS

CN    103392737 A    11/2013
EP    20082005812 A1    12/2008
(Continued)

*Primary Examiner* — John Weiss
(74) *Attorney, Agent, or Firm* — FMC Corporation

(57) ABSTRACT

Disclosed are methods of treating setts comprising (a) applying a coating of an alginate optionally containing one or more crop protection agents and/or one or more nutrients, and (b) crosslinking the alginate with a divalent metal ion. Also disclosed are compositions used in the disclosed methods of treating setts.

27 Claims, 14 Drawing Sheets

(51) Int. Cl.
  *C05G 3/00* (2006.01)
  *A01G 1/00* (2006.01)
  *C05D 9/02* (2006.01)
  *C09D 5/00* (2006.01)
  *C09D 5/14* (2006.01)
  *C09D 105/04* (2006.01)
  *A01N 47/40* (2006.01)
  *A01D 45/10* (2006.01)

(52) U.S. Cl.
  CPC ............... *C05D 9/02* (2013.01); *C05G 3/00* (2013.01); *C09D 5/00* (2013.01); *C09D 5/14* (2013.01); *C09D 105/04* (2013.01); *A01D 45/10* (2013.01)

(58) Field of Classification Search
  CPC . A01D 45/10; C05D 9/02; C09D 5/00; C09D 5/14; C09D 105/04; C05G 3/00
  See application file for complete search history.

(56) References Cited

U.S. PATENT DOCUMENTS

| | | | |
|---|---|---|---|
| 6,428,855 B1 * | 8/2002 | Kohno | A01C 1/06 427/212 |
| 6,521,452 B1 * | 2/2003 | Abdelrahman | A01H 4/005 435/410 |
| 7,921,598 B2 * | 4/2011 | Nishiyama | A01C 1/06 47/57.6 |
| 2010/0251434 A1 * | 9/2010 | Aramaki | A01C 1/00 800/320 |
| 2010/0251435 A1 | 9/2010 | Aramaki et al. | |
| 2010/0251436 A1 | 9/2010 | Aramaki et al. | |
| 2010/0257640 A1 | 10/2010 | Aramaki et al. | |
| 2010/0263095 A1 | 10/2010 | Aramaki et al. | |
| 2011/0172175 A1 * | 7/2011 | Chow | A01N 25/00 514/31 |
| 2011/0177146 A1 * | 7/2011 | Cahill | B05D 3/007 424/405 |
| 2012/0021911 A1 | 1/2012 | Majure et al. | |
| 2012/0282308 A1 * | 11/2012 | Chiu | A61K 8/733 424/401 |
| 2016/0007590 A1 * | 1/2016 | Schultz | A01C 1/06 47/57.6 |
| 2016/0205946 A1 * | 7/2016 | Stauffer | A01N 37/16 |

FOREIGN PATENT DOCUMENTS

| | | | |
|---|---|---|---|
| GB | 724435 | * | 2/1955 |
| WO | 2011048748 | A1 | 4/2011 |
| WO | 2012148529 | A1 | 11/2012 |

* cited by examiner

ALGINATE COATING FOR SETT TREATMENT

CROSS-REFERENCE TO RELATED APPLICATIONS

This application claims the benefit under 35 U.S.C. § 119(e) of U.S. Provisional Application Ser. No. 61/898,219, filed Oct. 31, 2013, the disclosure of which is incorporated herein by reference in its entirety.

FIELD OF INVENTION

The present invention relates to the field of agrochemical coatings for setts. The invention provides a method of sett coating using alginates, optionally containing insecticidal, nematocidal, or fungicidal active ingredients, and/or nutrients.

BACKGROUND OF THE INVENTION

Sugarcane is an important crop with a significant contribution in the food and renewable energy industries. However, the planting system with stalks and billets has evolved little since its establishment and expansion to different regions. Planting is the most expensive and important operation for sugarcane farms, and the success of the plant crop can affect yields to out the crop cycle, including multiple ratton crops. The traditional planting method demands a high quantity of stalks, ranging from 16 to 20 ton/ha for manual and mechanized planting respectively. This practice represents 30 to 40% of the planting costs and diverts stalks that otherwise would be used for sugar or alcohol production. According to estimates from the Center of Technology for Sugarcane (CTC), sugarcane mills with a renovation rate of 17% must dedicate around 5% of their planted area for the production of planting material. Generally, billets for conventional planting have around 35-40 cm with an average of 3 buds.

Although this expensive planting system with large amount of planting material represents a disadvantage, with big billets or whole stalks it is more likely to preserve moisture and nutrients and establish an adequate number of tillers compared to shorter billets, especially under dry weather conditions. In the past 3 years, alternatives using 5 cm mini-setts with one bud were tried. However, dependency of distant biofactories, reproduction issues, transportation on refrigerated containers and high sensitivity to unfavorable conditions made the system not commercially viable.

Various references discuss methods for growing sugarcane. For example, US 20100251434A1 provides a method for growing sugarcane, wherein one-node stem sections are treated to retain moisture with latex, paraffin and polymers coating. US 2010/0251435 provides another growing sugarcane method wherein at least one-node stem sections are stored at under 15° C. before being planted. US 20100251436A1 also provides a growing sugarcane method wherein only one-node stem sections, of about 2 to 12 cm, are treated with plant protection chemicals such as a fungicide, insecticide, miticide, termiticide, acaricide, molluscicide, nematicide, herbicide or plant activator.

Among the plant protection chemicals, US 20100251436A1 recites thiamethoxam, azoxystrobin, imidacloprid, fipronil, abamectin, clothianidin, chlorantraniprole, mefenoxam, fludioxonil and cyproconazole. US 20100257640A1 further provides a method of growing sugarcane plants based on the preparation of at least one-node cuts and subjecting them to a coating containing a binder, selected from the group consisting of polyvinyl acetates, polyvinyl acetate copolymers, and celluloses. EP 2005812A1 discloses a method for growing sugarcane based on planting cuts of one bud per stem sections, wherein compounds such as nutrients, fertilizers, micronutrient donors, biological agents, pesticides and/or safeners can be applied to the specified locus. However, none of these methodologies provide a robust and cost effective system for the industry. The present invention addresses this need.

BRIEF SUMMARY OF THE INVENTION

At least one aspect of the present invention is directed to a spray-based alginate sett coating process that uses two separate spray steps to introduce the alginate based coating onto the desired surface followed by the cross linking of the coating. Further, this technology prevents the loss of humidity in sugarcane setts. The process improves their tillering and sprouting potential. Sett biopolymer coating associated with insecticides, fungicides and nutrients enhances the overall health, pest and disease control efficacy, and nourishment of sugarcane plants.

According to this aspect of the invention, a sett treatment methodology is described that includes: (a) applying to setts a coating of an alginate, optionally containing one or more crop protection agents selected from the group consisting of insecticides, nematocides and fungicides, and/or one or more nutrients; and (b) applying to setts a coating of a divalent metal ion, thereby crosslinking the alginate with the divalent metal ion.

In one embodiment, the alginate is a soluble alginate selected from the group that includes sodium alginate and potassium alginate. In another embodiment, the divalent metal ion is selected from the group that includes $Ca^{+2}$, $Ba^{+2}$ and $Zn^{+2}$. In another embodiment, the divalent metal ion includes an aqueous solution of a divalent metal salt such as calcium or magnesium salts. Preferably, the divalent metal salt is a calcium salt, which is selected from the group that includes calcium chloride, calcium carbonate and calcium sulfate. In another embodiment, the divalent metal ion solution and the alginate coating are applied by spraying the setts. In another embodiment, the crop protection agent is selected from the group that includes Eternal® (Imidacloprid+Bifenthrin), Furadan 350 SC (Carbofuran), and Capture 400EC (Bifenthrin). In another embodiment, the nutrients are micronutrients selected from the group that includes Zn, Mo, and a combination thereof.

Another aspect of this invention is directed to sugarcane sett treatment methods including (a) spraying sugarcane setts with an aqueous calcium salt solution containing one or more crop protection agents selected from the group consisting of insecticides, nematocides and fungicides, and/or one or more nutrients, to form treated sugarcane setts; and (b) spraying said treated sugarcane setts with an aqueous solution of a soluble alginate to form coated sugarcane setts. In one embodiment, the crop protection agent is selected from the group that includes Imidacloprid and Bifenthrin, Carbofuran, and Bifenthrin. In another embodiment, the calcium salt is selected from the group calcium chloride, calcium carbonate and calcium sulfate. Preferably, the calcium salt is calcium chloride.

Another aspect of this invention is directed to a film composition used in the treatment of sugarcane setts, including (a) an alginate salt solution; and (b) a calcium salt solution, thereby forming a calcium alginate hydrocolloid.

In one embodiment, the alginate salt solution is selected from the group that includes sodium alginate and potassium alginate. Preferably, the alginate salt solution is sodium alginate. In another embodiment, the calcium salt is selected from the group that includes calcium chloride, calcium carbonate and calcium sulfate. Preferably, the calcium salt is calcium chloride. In one embodiment, the concentration of the alginate salt solution is about 0.05% to about 20% of alginate salt in water. Preferably, the concentration of the alginate salt solution is about 1%. In another embodiment, the concentration of the calcium salt solution is about 0.05% to about 20% of calcium salt in water. Preferably, the concentration of the calcium salt solution is about 1%.

In another aspect of the invention is directed to systems of enhancing larger sized plant products and increasing the yield of the product comprising (a) excising segments of the plant, (b) applying to said segment a coating of an alginate solution, optionally containing one or more crop protection agents selected from the group consisting of insecticides, nematocides and fungicides, and/or one or more nutrients; (c) applying to said segment a coating of a divalent metal ion, thereby crosslinking the alginate with the divalent metal ion and (d) planting said treated segments in a suitable environment to enhance product yield. The system may further include a suitable sprayer. The system of the present invention further includes timely harvesting and processing the sugarcane for follow up use.

DETAILED DESCRIPTION OF THE INVENTION

Figure 1:
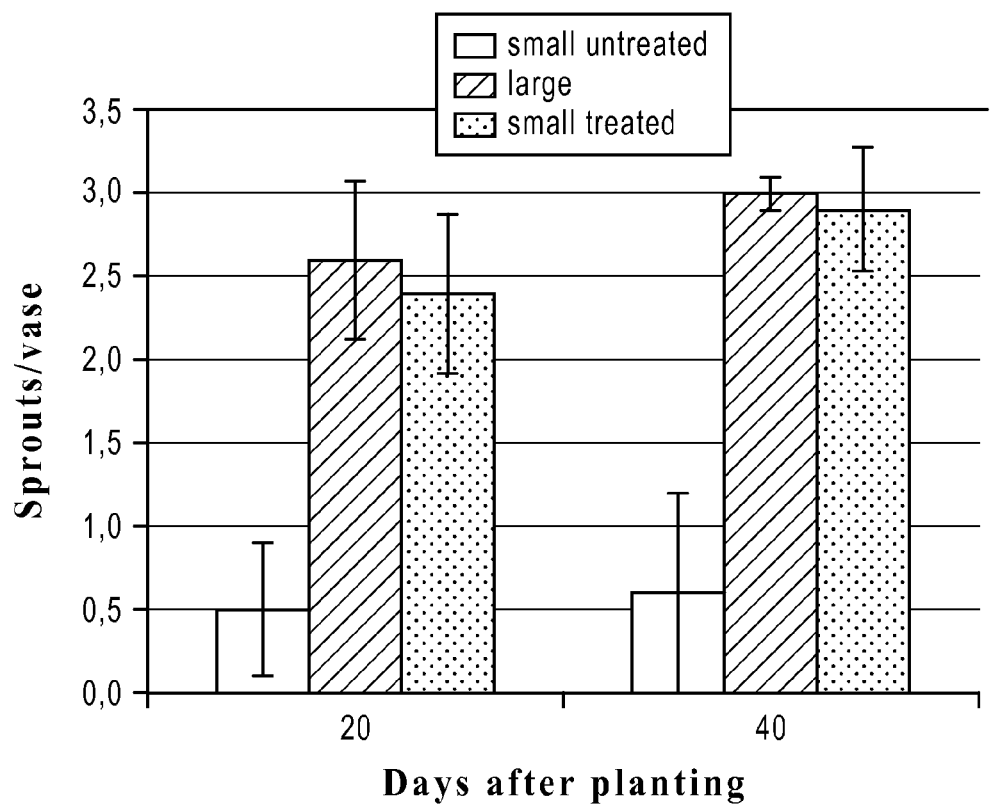
FIG. 1: A chart illustrating the average number of sprouts per experimental unit (three viable buds) of sugarcane setts without irrigation within seven days after planting, depending on the treatment: Small untreated—11 cm-sett without treatment; Large—3-buds large setts; Small treated—11 cm-sett with alginate.

This document is not limited to the particular methods, processes, compositions, or methodologies described, as these may vary. The technology used in the description is for the purpose of describing the particular versions or embodiments only, and it is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

As used in this document, the singular forms "a", "an", and "the" include plural reference unless the context clearly dictates otherwise. Thus, for example, reference to a "calcium salt" is a reference to one or more calcium salts and equivalents thereof known to those skilled in the art, and so forth.

As used in this document, the term "about" means plus or minus 10% of the numerical value of the number with which it is being used. Therefore, about 50% means in the range of 45% to 55%. As used in this document, the phrase "an effective amount" is meant to be read in light of the subject immediately related to the phrase as to the intended utilities. As such, "an effective amount" to cause crosslinking refers to any such concentration that facilitate formation of crosslinking. As such an effective amount can range between 0.01 moles up to about 25 moles of the suitable salt used to facilitate crosslinking.

As used herein, the phrase "sufficient time" refers to minimum amount of time required to achieve the intended purpose. For example, sufficient time of interaction between the alginate solution and salt include from 1 second to 30 minutes. In a similar manner, sufficient time to make alginate film include from 1 second to 30 minutes.

As used in this document, the term "comprises" or "comprising" means includes at least the following but does not exclude others.

The term "setts" or "sugarcane setts" as used in this document refers to stem cuttings or section of sugarcane, stalks or the like.

Alginate salts have been used for compositions in the treatment of plants for protection thereof. WO 2011US48748, CN 103392737 (A), and US 2012021911 (A1) describe plant treatment compositions comprising metal alginate salts and at least one amine compound useful in the treatment of plants, particularly food crops. U.S. Pat. No. 5,977,023 provides a pesticidal composition containing a water-insoluble alginate, which is prepared by treating a solid composition containing (a) a pesticidally active ingredient which is a pest-controlling active ingredient or a plant growth-regulating active ingredient and (b) an alginic acid or a water-soluble alginate with an aqueous solution containing a divalent or polyvalent cation which can convert said alginic acid or water-soluble alginate into a water-insoluble alginate.

Although several applications of alginate salts might have been described in prior art, the mechanisms of action of alginate is not well known. In fact, the use of alginate has not previously been demonstrated for application on sugarcane and other comparable plants.

In at least one aspect, the present invention provides processes and systems of protecting suitable segments of plants by applying sufficient amount of an alginate composition to a region of interest whereby limiting loss moisture and increasing germination. In one embodiment, the plant may be sugarcane, potato or sweet potato. In another embodiment, the plant is sugarcane and an alginate composition is applied to its respective open distal ends.

In another aspect, the present invention provides for process and systems of protecting sugarcane setts (root and shoot crops) by applying an alginate composition to a site or surface of interest and optimizing the amount of buds per linear meter needed to establish the plantation. In at least one embodiment, the site or surface of interest is smaller than 15 cm, including 12, 10, or 8 cm in length. In yet another embodiment, the surface of interest can be larger than 15 cm. The application of the alginate composition limits moisture loss while enhancing germination. As such at least one aspect of the present invention describes methods and a system of limiting or preventing moisture loss from the setts for at least an effective period of time and thereby increasing the rate of germination.

In another embodiment, the invention provides many other attributes and benefits to improve yield and production of the plant product. For example, in one embodiment the processes and systems according to the present invention increases buds' strength, reduces the operation for planting, and increases standability of the setts. In another embodiment, the present process and system provide for creating stronger emerged plants, reducing the area dedicated to planting material, and creating more stalks for sugar and alcohol production.

In yet another embodiment, the presently described process and system provides a growth promoting effect on the setts, and aids bettering crop protection from pests and diseases. In another aspect, the present invention provides a technology wherein sugarcane setts are treated with a composition that includes sodium alginate that when in contact with the target surface of the sett forms a crosslinked structure film. According to this aspect of the invention, the system provides a platform where a plant is processed through a harvester adapted to provide plant structures in sufficient size. In one embodiment, the plant is a sugarcane and the structure is the respective sugarcane setts. In another embodiment, the setts are cut to suitable sizes ranging from 2.5 cm to about 75 cm in length. In yet another embodiment, the setts are cut to sizes ranging from about 7.5 cm to about 45 cm. In a yet another embodiment, the setts are cut to sizes ranging from 10 cm to 15 cm in length.

In yet another aspect of the present system, a composition comprising sodium alginate for the treatment of sugarcane setts is provided. In one embodiment, the composition of the present disclosure can be applied directly to the setts of different or uniform sizes, or directly to the soil before or after planting, or both. In another embodiment, the setts are treated with the alginate solution and the crosslinker in sufficient amount of time for allowing the crosslinking so that a biofilm is formed at the distal ends of the respective setts.

In another embodiment, the present invention provides systems wherein the time between setts harvest and the application of the alginate is less than 48 hours, preferably less than 12 hours, and more preferably less than 6 hours. In another embodiment, the treated setts are stored in a cool dry place, out of direct sunlight. In another embodiment, the time between alginate coating and planting is less than 30, 20, 15, 10, 5, 2 minutes. In a preferred embodiment the time between alginate coating and planting is only in several seconds, including less than 80, 60, 40, and 20 seconds.

In another aspect, the alginate coating technology according to the present invention enables controlled release of pre-existing or newly-applied biological/chemical active ingredients on the sett surface. In another aspect, the presently described technology prevents loss of moisture in sugarcane setts, thereby improving emergence, germination and tillering. In one embodiment, the coating can be used in combination or contain effective amounts of insecticides, fungicides, nematicides, growth promoters and nutrients to enhance crop health and protection from pests and diseases. In such embodiment, crop protection compounds such as Imidacloprid, Bifenthrin, carbofuran, and Bifenthrin provide superior results when applied prior to the application of the alginate composition.

One aspect of the present invention is directed to a method of sett treatment including (a) applying to setts a coating of an alginate, optionally containing one or more crop protection agents selected from the group consisting of insecticides, nematocides and fungicides, and/or one or more nutrients; (b) applying to setts an effective amount of a divalent metal ion, and (c) crosslinking the alginate with the divalent metal ion to form a coating film/layer.

In one embodiment, the alginate is a soluble alginate selected from the group that includes sodium alginate and potassium alginate. In another embodiment, sodium alginate is the sodium salt of alginic acid, which is obtained by extraction from various species of deep-sea weed like Phaeophyceae. In another embodiment, the composition containing sodium alginate for the treatment of setts provides an increase of the speed of budding, viability of the buds to sprouting, germinating and tillering.

In yet another embodiment, the divalent metal ion is selected from the group that includes $Ca^{+2}$, $Mg^{+2}$, $Ba^{+2}$ and $Zn^{+2}$. In another embodiment, the divalent metal ion includes an aqueous solution of a divalent metal salt. Preferably, the divalent metal salt is a calcium salt, which is selected from the group that includes calcium chloride, calcium carbonate and calcium sulfate. In another embodiment, the divalent metal ion solution and the alginate coating are applied by spraying the setts in sufficient amounts to achieve effective and instant biofilm formation. In another embodiment, the alginate and metal salt are in sufficient amounts ranging from 0.01 to 25 moles. In another embodiment, the crop protection agent is selected from the group that includes Eternal® (Imidacloprid+Bifenthrin), Furadan 350 SC (Carbofuran), and Capture 400EC (Bifenthrin). In another embodiment, the nutrients are micronutrients, and can be selected from the group that includes Zn, Mo, and a combination thereof.

Another aspect of the present disclosure is directed to a process of sugarcane sett treatment including (a) spraying sugarcane setts with an aqueous calcium salt solution containing one or more crop protection agents selected from the group consisting of insecticides, nematocides and fungicides, and/or one or more nutrients, to form treated sugarcane setts; and (b) spraying said treated sugarcane setts with an aqueous solution of a soluble alginate to form coated sugarcane setts. In one embodiment, the suitable crop protection agent is selected from the group that includes Eternal® (Imidacloprid+Bifenthrin), Furadan 350 SC (Carbofuran), and Capture 400EC (Bifenthrin). Eternal®, Furadan 350 SC, and Capture 400EC. In another embodiment, the calcium salt is selected from the group that includes calcium chloride, calcium carbonate and calcium sulfate. Preferably, the calcium salt is calcium chloride.

In at least another aspect of the present invention, a novel method is described that comprises the steps of applying a layer of alginate solution to the sett, followed by applying a layer of the calcium salt solution. In at least this aspect of the invention, the process steps are part of a treatment system and are performed sequentially. In at least one embodiment, the treatment system may include a series of automated activities handled in separate units or compartments. For example, the process may begin by harvesting sugarcane to small setts for planting. As such the steps include selection of sugarcane fields for setts production, using specialized harvester to produce suitable sized setts, i.e. 12 cm setts, aiming at maximizing the number of setts with one bud, simultaneously or sequentially treating setts with either crop protecting agent, alginate compositions or combinations of both, providing setts carrier and treater, optionally applying other crop protection/enhancer products, and depositing the setts in-furrow, and finally closing of the furrow. In at least one preferred embodiment, the presently disclosed system provides an operational yield or gain of at least 2.5, 5, 10, 15, 18, 19, 20, or 25% when compared to a standard systems that does not employ the instant process steps.

In another aspect of the invention, systems of enhancing large scale plant products and increasing the yield of the plant product are described comprising (a) excising segments of the plant, (b) applying to said segment a coating of an alginate solution, optionally containing one or more crop protection agents selected from the group consisting of insecticides, nematocides and fungicides, and/or one or more nutrients; (c) applying to said segment a coating of a divalent metal ion, thereby crosslinking the alginate with the divalent metal ion and (d) planting said treated segments in a suitable environment to enhance product yield. The system of the present invention further includes timely harvesting and processing the sugarcane for follow up use. In one embodiment, the plant product is a sugarcane sett or a segment of sweet potato.

In one embodiment, the degree of crosslinking has a reverse correlation with the loss of moisture. In another embodiment, the time sufficient to achieve desirable crosslinking is less than 30 minutes, 10 minutes or even between 5 to 80 seconds, In another aspect of the present invention, pretreated setts are provided for direct commercial use. According to this aspect of the invention, setts can be pretreated with suitable fungicides, insecticides, nematicides, growth promoters and the like and be used directly. In another embodiment, such pretreated setts can further be treated before coating with the alginate.

In another embodiment, pre-treated setts are coated with a layer of alginate coating to introduce a controlled release property to the active ingredients ("AI") that have already been included in the pretreatment steps. In at least one embodiment, the process includes spraying the alginate solution (i.e., without the AI mixed) onto the sett surface followed by spraying an effective amount of a calcium salt to facilitate sufficient degree of crosslinking. As such, the introduction of a controlled release property to the AI on the pretreated setts can be achieved using the crosslinked alginate resulting from the two-step spray process described above.

In another embodiment, the process steps follow an alternative sequence. In such embodiment, first the calcium salt material is applied on the sett surface first and then the alginate coating solution will be applied to the same area. In one embodiment, the alginate salt solution is selected from the group that includes sodium alginate and potassium alginate. Preferably, the alginate salt solution is sodium alginate. In another embodiment, the calcium salt is selected from the group that includes calcium chloride, calcium carbonate and calcium sulfate or any mixtures thereof; but preferably, the calcium salt is calcium chloride.

Another aspect of the present disclosure is directed to a film composition used in the treatment of sugarcane setts, including (a) an alginate salt solution; and (b) a calcium salt solution, thereby forming a calcium alginate hydrocolloid. In one embodiment, the alginate salt solution is selected from the group that includes sodium alginate and potassium alginate. Preferably, the alginate salt solution is sodium alginate.

In yet another embodiment, the calcium salt is selected from the group that includes calcium chloride, calcium carbonate and calcium sulfate. Preferably, the calcium salt is calcium chloride. In one embodiment, the concentration of the alginate salt solution is about 0.05% to about 20% of alginate salt in water. Preferably, the concentration of the alginate salt solution is about 1%. In another embodiment, the concentration of the calcium salt solution is about 0.05% to about 20% of calcium salt in water. Preferably, the concentration of the calcium salt solution is about 1%.

In all aspects of the present disclosure, different concentrations of the alginate and the calcium salt can be used in the coating process to adjust the release rate of the resultant sett coating.

In all aspects of the present disclosure, the addition of functional agents, or crop protection agents, to alginate solution can also be employed in the alginate coating formulations. Such functional agents include, but are not limited to, nutrients, micronutrients, insecticides, nematocides and fungicides.

Those of ordinary skill in the art can appreciate that the coating thickness and the concentrations of the AI in the formulations may be adjusted to fit the need. Similarly those of ordinary skill in the art can appreciate that at least one advantage of the present technology is to limit the loss of moisture in sugarcane setts, thereby improving their tillering and sprouting potential.

In another aspect, the presently described invention provides for an innovative sugarcane plantation concept with a reduced number of seedlings and optimized operational capacity, in addition to allowing the development of smaller and lighter equipment. A sett biopolymer coating associated with insecticides, fungicides, growth promoters and nutrients enhances the overall health, pest and disease control efficacy, and nourishment of sugarcane plants. In at least one embodiment, the system and process steps described herein provides an operational yield of at least 10%, 15%, 20% higher than any comparative system that does not employ said alginate composition in the manner described herein.

In all aspects of the present disclosure, the coating formulations can be prepared by mixing milled pesticide particles directly into a sodium alginate solution, or adding sodium alginate to the existing SC formulations of the pesticides. This coating formulation can be then applied to the sett surface via spray. A suitable apparatus capable of coating/spraying can be used in the presently disclosed systems and processes. One such commercial seed treater is the "Wintersteiger Hege 11 Seed Treater". After spray application of the pesticide/alginate seed coating, a water solution of $CaCl_2$ is then sprayed onto the seed coating surface to introduce the crosslinking of the coating.

In all aspects of the present disclosure, solutions are applied using various methods, including but not limited to, a spraying method over the sugarcane sett or plantation furrow, and an immersion method in two or more steps. The immersion method includes immersing the sett to be treated in one solution, then immersing the sett in subsequent solutions. Smaller plant products may be a better fit for such sequence of steps. The smaller plants are typically those that have one bud as opposed to 2 or 3 buds.

The system and the technology described herein reduces the number of sugarcane seedlings to be planted, since it generates a larger quantity of viable buds obtained from a single harvesting area. The reduction of seedling length and protection against the loss of moisture in setts, associated to an enhanced interaction from insecticides and fungicides applied with this technology to treat sugarcane setts, resulted in a more efficient, economic, sustainable, and effective plantation system, with regard to pest and disease management.

Those of ordinary skill in the art can appreciate that sugarcane typically requires a large amount of biological material to sustain propagation by stems, averaging 16 ton/ha for manual plantation and 20 ton/ha for mechanized plantation operations. As a result, sugarcane seedling costs to form new sugarcane fields are extremely high, accounting for approximately 30% to 40% of the new sugarcane field's total cost. Another limiting factor regarding plantation operation is the workforce demand, which is increasingly restricted in agricultural production systems.

At least one aspect of the present invention provides for systems and processes that enhance the quantity of buds per linear meter (in the sugarcane field implementation). In one embodiment, the present invention maximizes the potential of buds; reduces the activity and movement of machines in the land; reduces the number of operations during plantation; maximizes the uniformity of emerging plants; and the potential of emerged plants. In yet another embodiment, the present invention reduces the sugarcane cultivation area destined to produce seedlings, thus increasing the area used to produce sugar and alcohol. In another embodiment, the process of the present invention provides further protection of plants against pests, nematodes, and diseases.

EXAMPLES

Example 1. Effects of Alginate Treatment of Sugarcane Setts in Relation to Sprouting, Viability of Buds, and Tillering The use of the present technology in the treatment of sugarcane setts with alginate provides a gain in speed of sprouting as noted in Table 1. Table 1 provides average number sprouts and tillers per experimental unit (10 setts) and shoot length of sugarcane due to the application of alginate technology on 11 cm-cuts Variety RB 867515, Uberlandia-MG Brazil, 2013.

TABLE 1

| Alginate Treatment on | Sprouts, Tillers/10 setts | | | Shoot length (cm) | |
| --- | --- | --- | --- | --- | --- |
| 11 cm-cuts | 20 DAP | 40 DAP | 60 DAP | 40 DAP | 60 DAP |
| Control (No Alginate) | 5.8 | 6.6 | 10.2 | 24 | 44 |
| Alginate (0.5%) | 8.8 | 9.6 | 15.6 | 39 | 65 |
| Alginate (1.0%) | 8.8 | 9.4 | 15.8 | 40 | 66 |
| Alginate (2.0%) | 8.8 | 9.6 | 15.8 | 39 | 67 |
| CV (%) | 7.61 | 5.78 | 6.61 | 12.92 | 6.08 |

At 20 days after planting ("DAP"), treatments with alginate resulted in 8.8 sprouts/10 setts, being superior to control (without alginate treatment) with 5.8 sprouts. Following the process steps according to the present invention provided conditions for the vegetative propagation material to have greater viability of buds. This can be observed from the best budding at 40 DAP, where treatments with alginate have 94-96% sprouting while the control has 66%.

The application of alginate to sugarcane setts improved the tillering thereof, as observed at 60 DAP. The present alginate technology provides 15.6 to 15.8 tillers/10 setts, being higher than what is observed in the control, resulting in 10.2 tillers/10 setts. This technology also enhances the development of shoots from buds and tillers, as can be seen in Table 1 at 40 and 60 DAP, respectively.

The response in the increasing of the speed of sprouting, viability of buds for and tillering was not affected by the concentration of alginate solution for the treatment of setts, as can be seen in Table 1.

The alginate treatment of the present invention is also beneficial for protecting setts from moisture loss, thereby improving conditions for the viability of buds, better sprouting and tillering of sugarcane, as well as the best development of the shoots and tillers. This protective action of moisture loss from the setts to the soil is observed even when small setts are planted in soil with suitable moisture availability conditions. Under these conditions, as shown in Table 1, the effect is observed with an increasing of the speed of sprouting, increased vigor of sprouting buds and better tillering, as well as better development of sugarcane shoot.

Those of ordinary skill in the art can appreciate that when small setts were planted in dry soil and irrigation occurred two days after planting, this protective effect against moisture loss from the setts to the soil provides faster sprouting, better viability of sprouting buds and tillering, and better development of sugarcane shoots. Table 2 clarifies this affect by indicating improved average number of sprouts and tillers per experimental unit (10 setts) and shoot length of sugarcane due to the application of alginate technology on 11 cm-setts. Variety RB 86 7515, Uberlândia—MG/Brazil, 2013.

TABLE 2

| Alginate Treatment on | Sprouts, Tillers/10 setts | | | Shoot length (cm) | |
|---|---|---|---|---|---|
| 11 cm-cuts | 20 DAP | 40 DAP | 60 DAP | 40 DAP | 60 DAP |
| Control (No Alginate) | 6.2 | 7.0 | 12.4 | 24.6 | 44.4 |
| Alginate (0.5%) | 9.0 | 10.0 | 16.4 | 42.6 | 79.2 |
| Alginate (1.0%) | 9.2 | 9.8 | 16.2 | 44.6 | 80.0 |
| Alginate (2.0%) | 9.0 | 9.8 | 16.2 | 44.2 | 79.8 |
| Alginate (3.0%) | 9.0 | 9.8 | 16.0 | 43.8 | 80.4 |
| 'LSD (P = .05) | 0.68 | 0.54 | 1.25 | 2.62 | 4.85 |
| CV (%) | 6.01 | 4.31 | 6.02 | 4.89 | 4.97 |

Means followed by the same letter in the column do not differ by Duncan's test at 5% probability.

The application of alginate on small setts of sugarcane surprisingly improved speed of sprouting (9.0 to 9.2 sprouts/ 10 setts) at 20 DAP compared to the control without alginate (6.2 sprouts/10 setts) as shown in Table 2. The technology also provided conditions for the vegetative propagation material to have greater viability of buds that can be observed from the best sprouting at 40 DAP, where treatments with alginate have 98-100% of sprouting while the control has 70%. As such the treatment provides 30% more sprouting than the control. In a more preferred embodiment, the treatment are designed to provide more than, 40%, 50% or 60% sprouting than the non-treated setts.

The application of alginate to sugarcane setts improved the tillering, as observed at 60 DAP. The present alginate technology provided 16.0 to 16.4 tillers/10 setts, being higher than the observed in the control with 12.4 tillers/10 setts. This technology also enhanced the development of shoots from buds and tillers, as shown in Table 1 at 40 and 60 DAP, respectively.

Even during drought stress at planting time (two days without moisture) the response of increased sprouting speed, viability buds and tillers was not affected by the concentration of alginate solution (0.5% to 3.0%) for the treatment of setts, as shown in Table 2.

The small setts (9 to 15 cm) are more sensitive than large setts (comprising 3 buds) to the loss of moisture in the soil and, consequently, have reduced vigor and viability of buds for sprouting and tillering, as shown in Table 3.

The planting small setts, without using alginate to protect the setts from moisture loss, under commercial area conditions, provided smaller sprouting and tillering, even in irrigated soil conditions prior to planting (two layers—one of 40 and one 20 mm) and irrigation after planting (two layers of 20 mm). The propagation material split into smaller setts had greater surface contact with the soil and less protection conditions for the loss of moisture to the soil. These conditions caused lower vigor and viability of buds that is expressed in lower sprouting and tillering of sugarcane, as shown in Table 3. Table 3 provides an average number of sprouts and tillers per meter depending on the planting of large setts (3 buds) and small setts (11 cm) without applying alginate technology. Variety CTC 02, Guaira—SP/Brazil, 2014.

TABLE 3

| Treatments | Sprouts/meter 35 DAP | Tillers/meter 113 DAP |
|---|---|---|
| Control (Sugar mill pattern 3 buds-setts) | 4.1 | 22.8 |
| Small setts without alginate treatment | 2.7 | 12.4 |

Larger setts (3 buds) have a greater ability to protect the buds from the moisture loss to the soil, and the greater fractionation of sugarcane propagation material depends on modifying said moisture loss condition with the addition of a product to reduce this moisture loss. The alginate provided this protection from moisture loss and better vigor and viability of sugarcane buds, improving sprouting, tillering and shoot growth of sugarcane.

The effect of protection against moisture loss of large setts (3 buds) can be seen in FIG. 1, where it provided 100% sprouting at 40 DAP, even when subjected to water stress for 7 days after planting. The addition of alginate in small setts provided similar protection conditions to that of large setts having 3 buds, providing 98% of sprouting in the same period. The small sett was very sensitive to moisture loss, as shown in FIG. 1, with 17% of sprouting. The addition of alginate onto small setts was efficient to provide protection from moisture loss and to ensure certainty as to the viability of such large setts having 3 buds.

Figure 2:
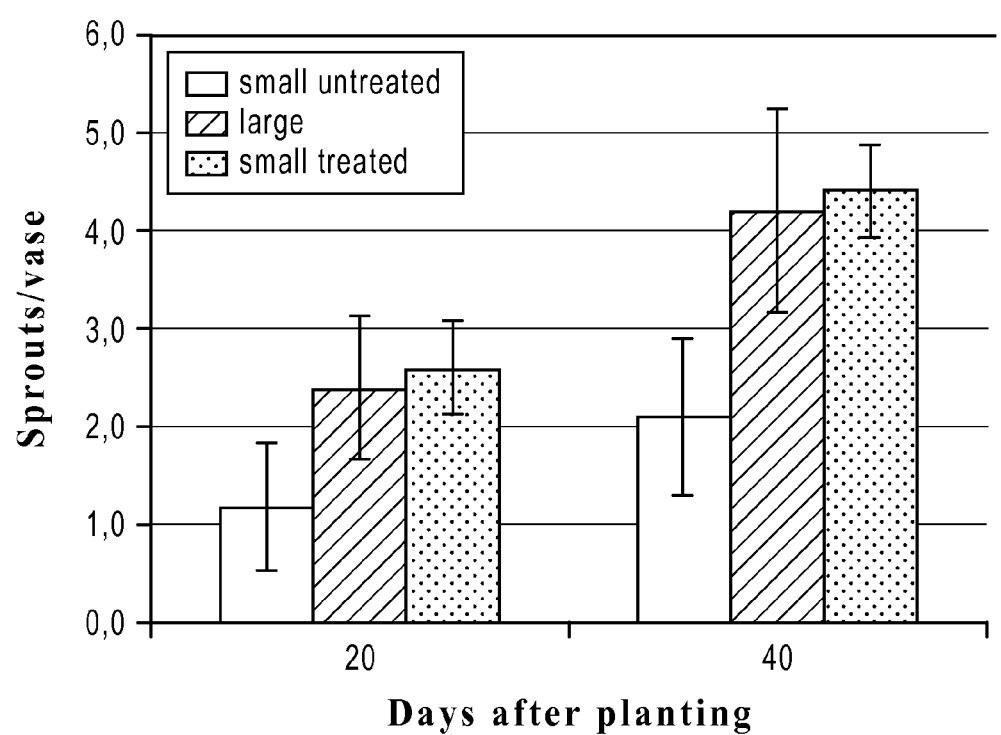
FIG. 2: A chart illustrating the average number of sprouts per experimental unit (three viable buds) of stalks of sugarcane without irrigation within seven days after planting, depending on the treatment: Small untreated—11 cm-sett without treatment; Large—3-buds large setts; Small treated—11 cm-sett with alginate.

The response of the protection to moisture loss provided by alginate in the treatment of small setts was observed in experiments with the induction of water stress of 7 days after planting sugarcane varieties RB 86 7515 and RB 92 579, as shown in FIGS. 1 and 2. The response observed in RB 92 579 variety was similar to that observed in RB 86 7515.

The alginate coat treatment of small sugarcane setts also provided protection to tillering buds, as observed in FIG. 2. The large sett containing 3 buds had 4.2 tillers/3 buds at 40 DAP, thus being similar to small sett treated with alginate (4.4 tillers/3 buds).

Figure 3:
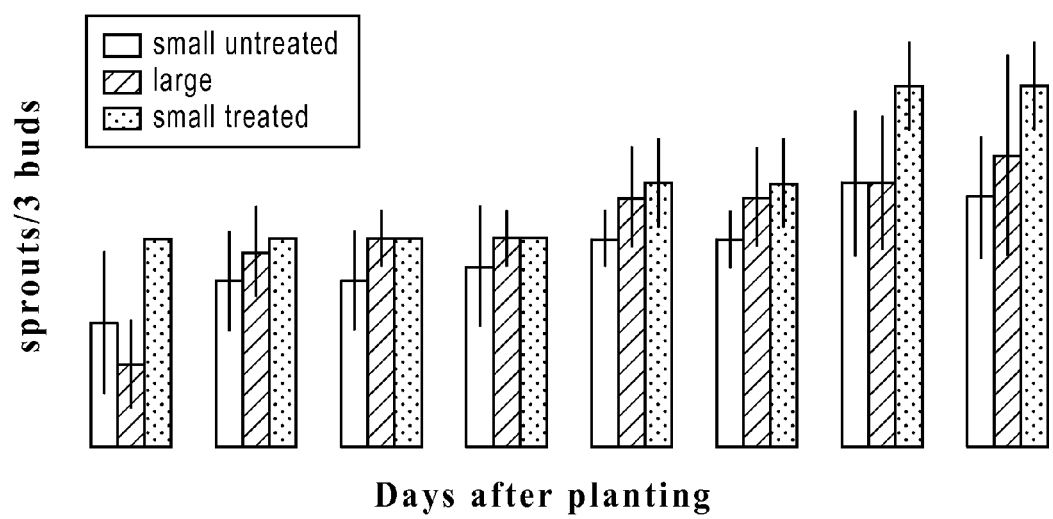
FIG. 3: A chart illustrating the average number of sprouts per experimental unit (three viable buds) of setts of sugarcane without irrigation within one day after planting, depending on the treatments: Small untreated—11 cm-sett without treatment; Large—3-buds large setts; Small treated—11 cm-sett with alginate.
Figure 4:
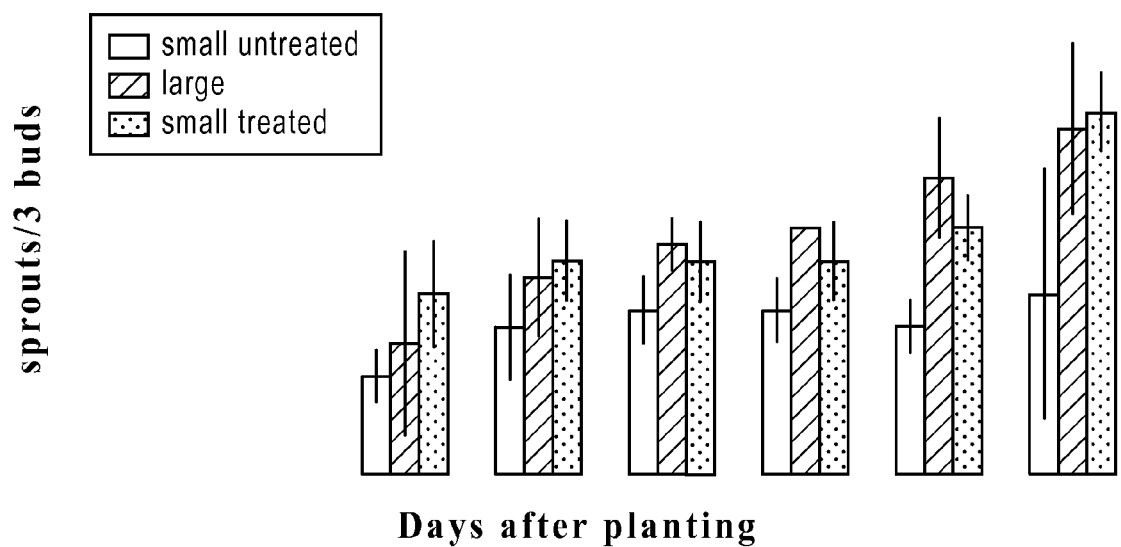
FIG. 4: A chart illustrating the average number of sprouts per experimental unit (three viable buds) of stalks of sugarcane without irrigation at the interval of six days after planting, depending on the treatments: Small untreated—11 cm-sett without treatment; Large—3-buds large setts; Small treated—11 cm-sett with alginate.
Figure 5:
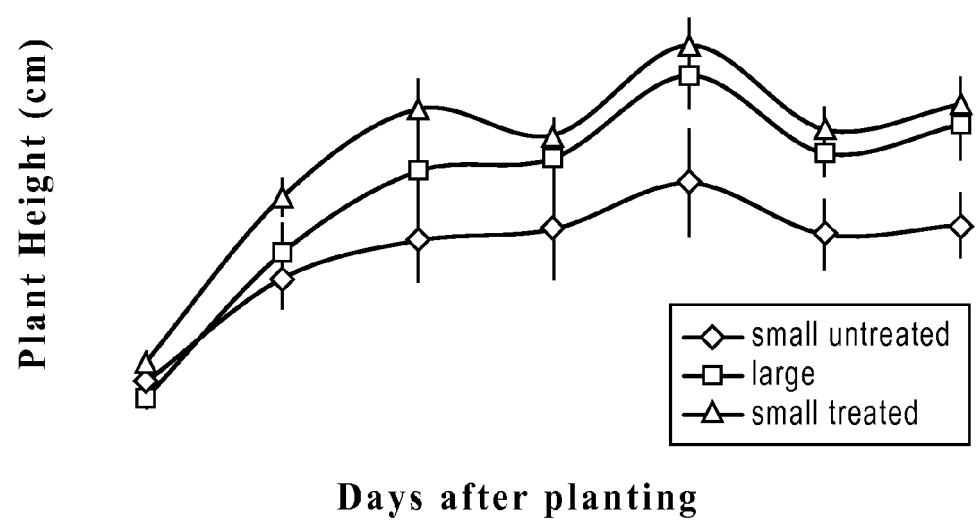
FIG. 5: A chart illustrating the average shoot length of cane sprouts without irrigation within one day after planting, depending on the treatments: Small untreated—11 cm-sett without treatment; Large—3-buds large setts; Small treated—11 cm-sett with alginate.
Figure 6:
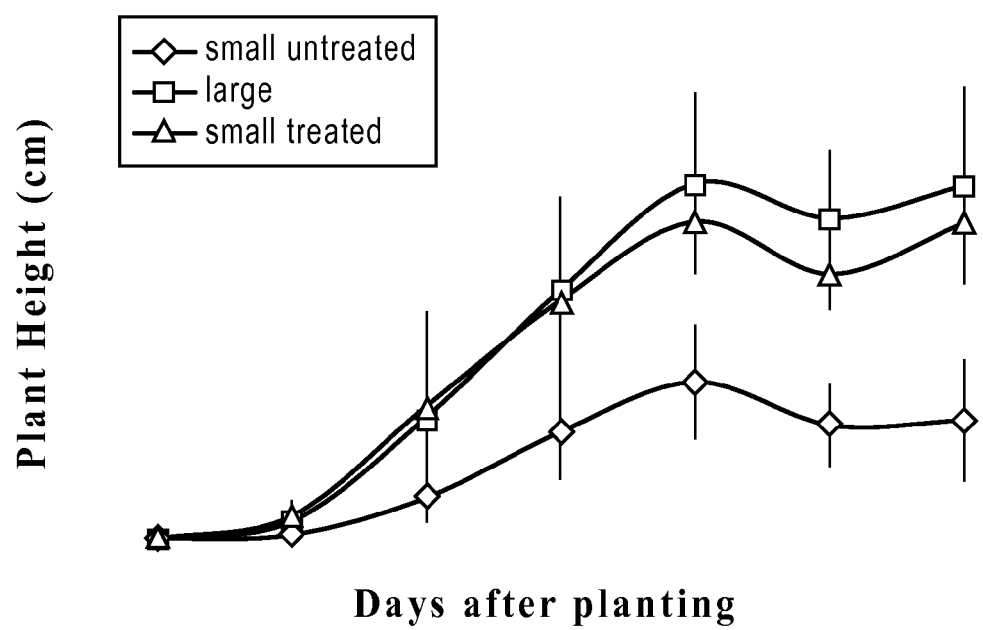
FIG. 6: A chart illustrating the average shoot length of cane sprouts without irrigation at intervals of six days after planting, depending on the treatments: Small untreated—11 cm-sett without treatment; Large—3-buds large setts; Small treated—11 cm-sett with alginate.
Figure 7:
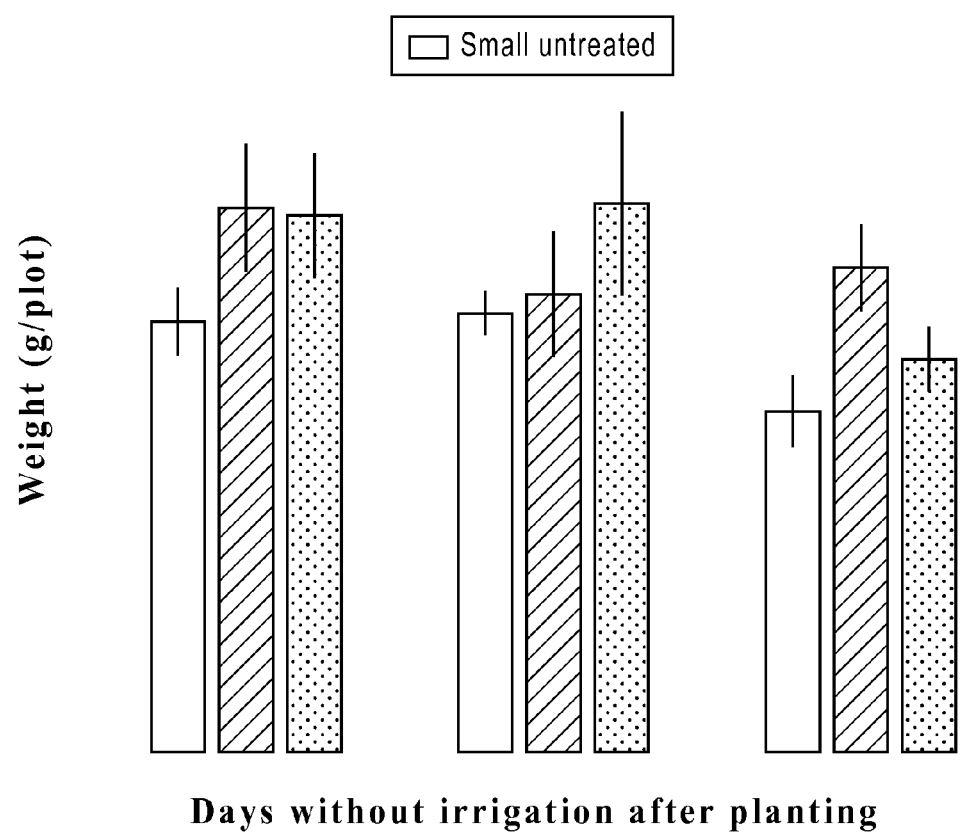
FIG. 7: A chart illustrating the average weight of sugarcane without irrigation at intervals of one, two and seven days after planting, depending on the treatments: Small untreated—11 cm-sett without treatment; Large—3-buds large setts; Small treated—11 cm-sett with alginate.
Figure 8:
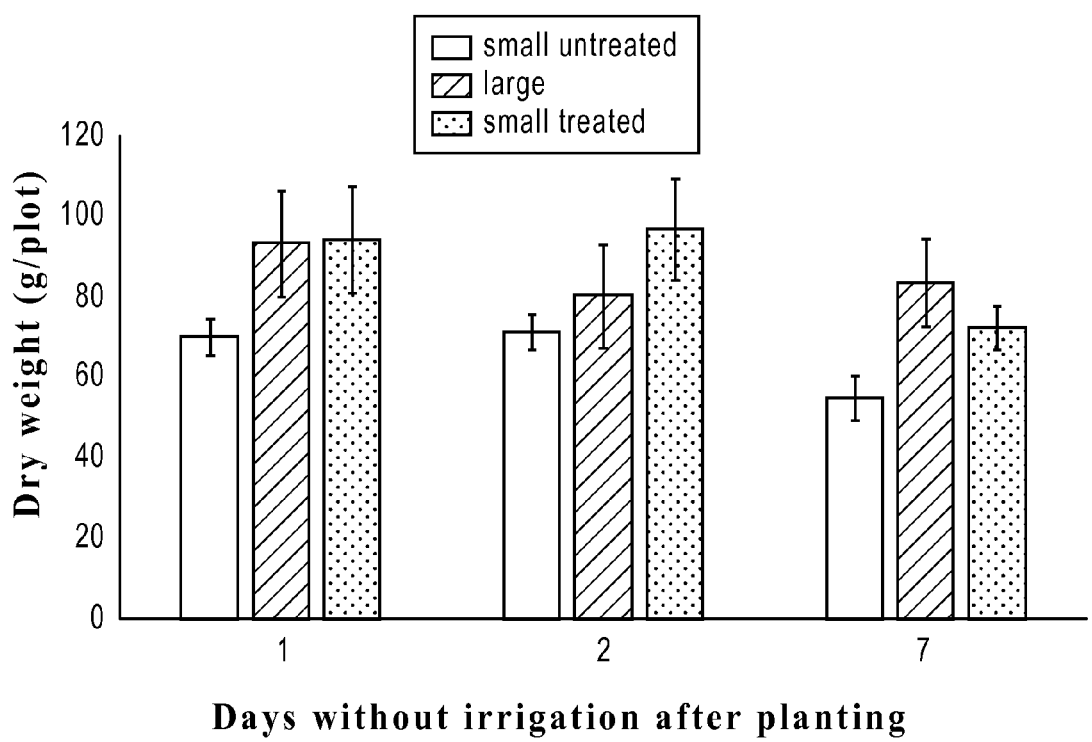
FIG. 8: A chart illustrating the average dry weight of sugarcane without irrigation at intervals of one, two and seven days after planting, depending on the treatments: Small untreated—11 cm-sett without treatment; Large—3-buds large setts; Small treated—11 cm-sett with alginate.
Figure 9:
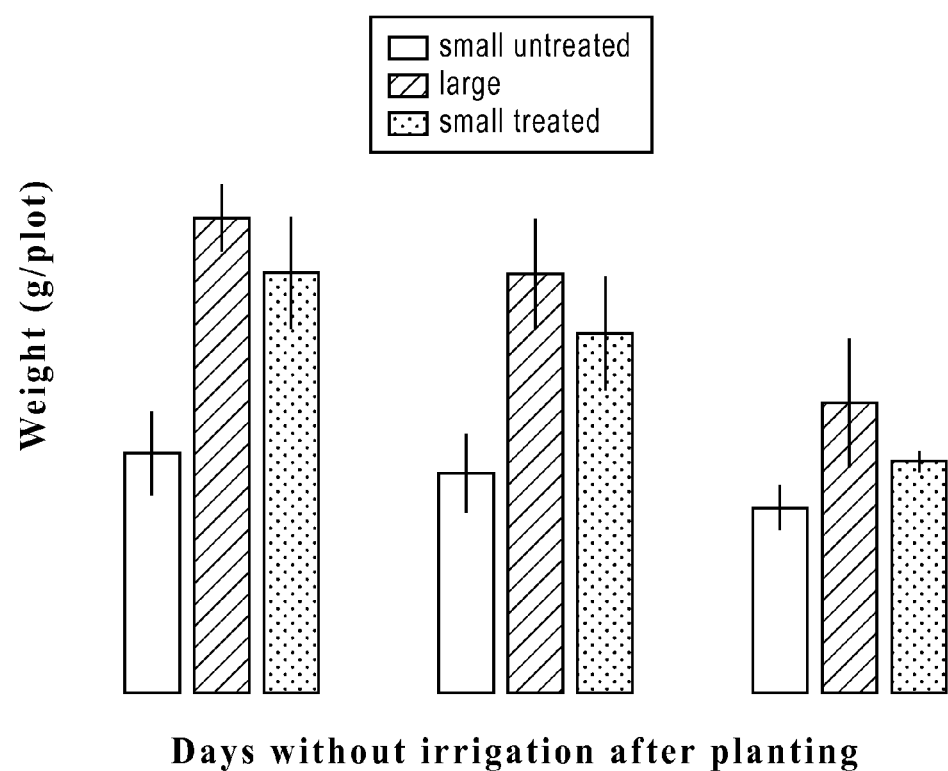
FIG. 9: A chart illustrating the average weight of sugarcane without irrigation at intervals of one, two and seven days after planting, depending on the treatments: Small untreated—11 cm-sett without treatment; Large—3-buds large setts; Small treated—11 cm-sett with alginate.
Figure 10:
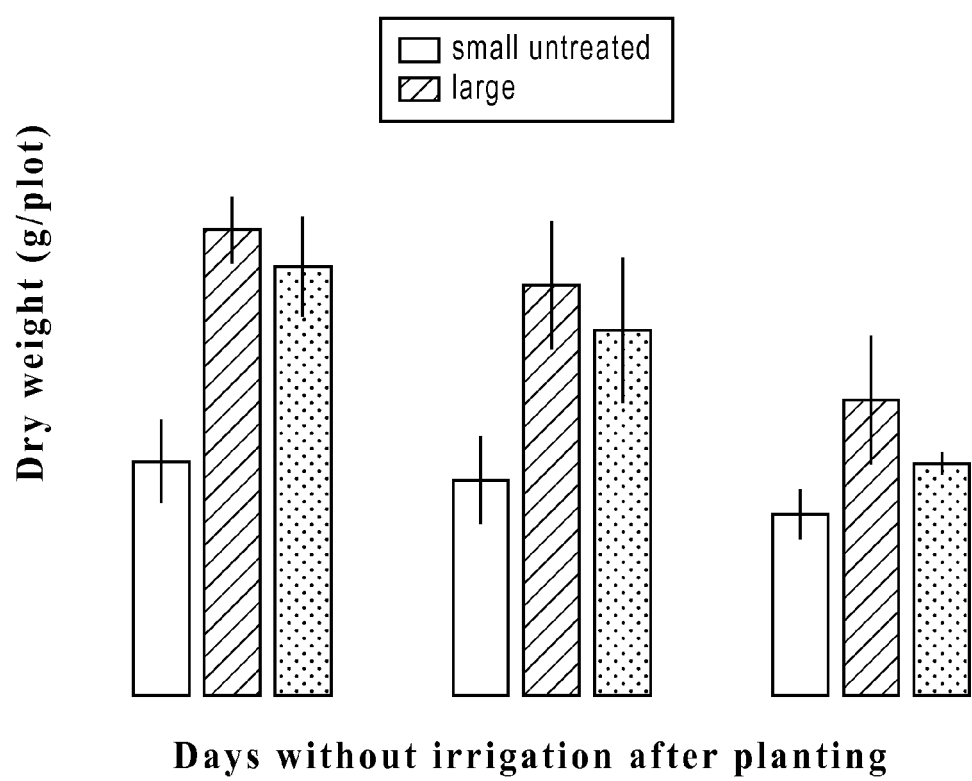
FIG. 10: A chart illustrating the average dry weight of sugarcane without irrigation at intervals of one, two and seven days after planting, depending on the treatments: Small untreated—11 cm-sett without treatment; Large—3-buds large setts; Small treated—11 cm-sett with alginate.

The small setts treatment with alginate also provided protection tillering buds. This can be observed in FIGS. 3 and 4. Alginate in the treatment of small setts of sugarcane also provided enhanced shoot growth, as can be seen in FIGS. 5 and 6. Even on drought stress of just 1 day after planting, the addition of alginate in the treatment of setts provided larger plants than the big setts of 3 buds did from 4 to 41 DAP. The small setts without alginate treatment lost moisture and buds' strength, resulting in smaller plants, even in the condition of only one day of drought after planting, as shown in FIG. 5. When water stress conditions were severe (6 days without irrigation after planting), the differences were greater, and plants originated from untreated small setts (without alginate) resulted in lower vigor/strength and growth compared with plants derived from buds of small setts treated with alginate, as observed in FIG. 6.

The addition of alginate onto sugarcane small setts was efficient to provide protection against moisture loss and to ensure certainty as to the feasibility of the buds such as that of big setts of 3 buds and the best condition for the growth of plants originated from these buds.

Alginate in the treatment of small setts of sugarcane also provided better plant development, as can be seen in FIGS. 7, 8, 9 and 10. Small setts without alginate treatment resulted in lighter plants, even in the condition of only one day of drought after planting. Regardless of the sugarcane variety and severity of drought stress, plants formed from setts treated with alginate always showed better development (weight and dry weight) than plants from untreated small setts, as observed in FIGS. 7, 8, 9 and 10.

Example 2: The Addition of Insecticides to the Treatment with Alginate

The addition of insecticides to the treatment of sugarcane setts provides operational and assertiveness gains of the application of the method in view of the increased contact of said insecticides with setts and greater protection for pest control at planting.

The insecticides had different response regarding the interaction with sugarcane setts, as can be seen in Tables 4 and 5.

The insecticides Eternal, Furadan 350 SC and Capture 400EC possessed excellent interaction with setts and provide appropriate conditions for sugarcane growth and tillering, as shown in Tables 4 and 5. Talisman (Bifenthrin+Carbosulfan) and Marshal Star (Carbosulfan) on the other hand did not. Table 4 provides an average number of Tillers per experimental unit (2 setts) and sugarcane shoot length due to the treatment applied to sugar cane setts (11 cm) with insecticides and later alginate technology. Variety RB 86 7515, Uberlândia—MG, 2014.

TABLE 4

| Treatments to | Tillers/2 setts | | | Shoot length (cm) | |
|---|---|---|---|---|---|
| 11 cm-setts | 15 DAP | 30 DAP | 52 DAP | 30 DAP | 52 DAP |
| Control (Alginate) | 1.6 | 1.6 | 1.6 | 20.2 | 26.4 |
| Eternal (4 L/ha) & Alginate | 1.6 | 2.0 | 2.0 | 23.2 | 30.8 |
| Talisman (5 L/ha) & Alginate | 0.2 | 0.2 | 0.6 | 5.2 | 17.0 |
| Furadan 350 SC (7 L/ha) & Alginate | 1.0 | 1.6 | 1.6 | 21.0 | 32.8 |
| Marshal Star (4 L/ha) & Alginate | 0.2 | 0.4 | 0.2 | 7.0 | 2.0 |
| Capture 400EC (1 L/ha) & Alginate | 0.6 | 1.2 | 1.4 | 24.6 | 33.2 |
| Control (No Alginate) | 1.2 | 1.2 | 1.4 | 15.6 | 20.7 |
| CV (%) | 63.6 | 53.18 | 53.08 | 50.21 | 67.54 |

Table 5 provides average number of tillers per experimental unit (4 setts) and sugarcane shoot length due to the treatment of sugarcane setts (11 cm) with insecticides and later alginate technology. Variety RB 86 7515, Uberlândia—MG, 2014.

TABLE 5

| Treatments to | tillers/4 setts | | | Shoot length (cm) | |
|---|---|---|---|---|---|
| 11 cm-setts | 20 DAP | 40 DAP | 60 DAP | 40 DAP | 60 DAP |
| Control (Alginate) | 4.0 | 4.0 | 5.2 | 31.4 | 47.0 |
| Eternal (4 L/ha) & Alginate | 4.0 | 4.0 | 5.6 | 38.0 | 63.0 |
| Talisman (5 L/ha) & Alginate | 2.6 | 2.6 | 3.6 | 30.4 | 43.0 |
| Furadan 350 SC (7 L/ha) & Alginate | 2.6 | 3.6 | 5.4 | 34.0 | 67.0 |
| Marshal Star (4 L/ha) & Alginate | 2.2 | 2.2 | 3.2 | 22.0 | 47.0 |
| Capture 400EC (1 L/ha) & Alginate | 2.6 | 3.4 | 5.4 | 30.0 | 66.0 |
| Control (No Alginate) | 2.6 | 3.6 | 4.4 | 26.6 | 45.0 |
| CV (%) | 18.16 | 14.23 | 13.82 | 13.37 | 8.58 |

The sequence of adding insecticide during the treatment of sugarcane setts also had an impact in the outcome. The insecticide Eternal, when applied prior to the application of alginate to the setts, was effective in maintaining the potential of sprouting and tillering of sugarcane, as shown in Tables 4, 5 and 6. When Eternal was applied together with alginate, smaller sprouting, tillering, and growth of sugarcane was observed, and therefore lowered the productivity of the crop, as shown in Table 6. Table 6 provides average results of sprouts, tillers, and culms of sugarcane per meter and TCH (biometrics) as a function of the treatment of sugarcane setts (11 cm) with the technology of alginate and insecticide. Variety CTC 02, Guaira—SP, 2014. As such it appears that sequence of applying the insecticide plays an important role in the final treatment outcome. As such, the unexpected observation provides that application of insecticides prior to the alginate composition significantly improves the efficacy of the treatment system as compared to the mixing of the insecticide with the alginate composition.

TABLE 6

| Trt No. | Sett Type | Sett Treatment | In Furrow Treatment | Rate L/ha | Sprouts, 34DAP | Tillers 45 DAP | Ou 113 DAP | Culms/meter 252 DAP | Yield (tons) 252DAP |
|---|---|---|---|---|---|---|---|---|---|
| 1 | 3 buds | None | Eternal | 3.00 | 2.9 | 4.8 | 24.7 | 18.2 | 124.9 |
| 2 | Small | None | Eternal | 3.00 | 4.2 | 7.4 | 31.7 | 19.8 | 124.5 |
| 3 | Small | Alginate | Eternal | 3.00 | 4.5 | 6.4 | 31.5 | 19.8 | 134.4 |
| 4 | Small | Eternal before Alginate | None | 3.00 | 4.7 | 6.5 | 32.7 | 18.5 | 135.6 |
| 5 | Small | Alginate + Eternal | None | 3.00 | 2.4 | 4 | 24.3 | 15.9 | 106.1 |
| 6 | Small | None | Alginate | 0.00 | 6.2 | 9 | 39.1 | 19.6 | 126.9 |
| 7 | Small | None | Alginate + Eternal | 3.00 | 6.3 | 9.5 | 43 | 17.2 | 117.1 |
| 8 | 3 buds | None | None | 0.00 | 3.8 | 4.8 | 24.4 | 17.6 | 117.7 |
| | CV (%) | | | | | 18.65 | 12.33 | 10.52 | 7.97 | 11.24 |

Another surprising observation is the impact of such sequence in efficacy of the insecticides Marshal Star and Talisman. Marshal Star and Talisman caused reduction of sugarcane sprouting, as shown in Tables 4 and 5. However, when applied to setts before said setts being treated with alginate, they did not cause injury to the setts. These insecticides when applied on the planting furrow directly to the setts did not cause injury, even if setts were treated with alginate.

Those of ordinary skill in the art can appreciate that the present alginate technology for treatment of sugarcane setts with alginate provided better sprouting, tillering and development of the sugarcane crop, resulting in higher yields TCH (tons of cane per hectare), as shown in Table 6. The use of present alginate technology increased sugarcane yields in 8.6% compared to the control, based on planting with large stalks with 3 buds, and sugarcane yields 135.6 TCH, being 8.6% higher than control, based on planting with large stalks of 3 buds, that produced 124.9 TCH.

In addition, the results of Table 6 provides that sugarcane crop had a response with respect to planting density that needs to be considered during the treatment. As the present alginate technology had improved sprouting and tillering and the density of buds at planting was 20 buds/meter, this being suitable for the planting of big setts of 3 buds, the treatments with the addition of alginate, in the treatment of setts and planting furrow, had been harmed.

As can be observed in treatments 6 and 7, with the addition of alginate into the planting furrow, even with about 2 times more sprouts and tillers compared to control, (planting of 3-buds cuttings), in biometrics held 252 days after, treatment 7 had fewer culms per meter than the control and treatment 6 despite having more culms per meter than the control. This observation demonstrates that the yield is not proportional to the amount of culms. At least one explanation of this occurrence can be in that the sugarcane crop had a balance of plant density per meter and, when in higher densities, a competition occurred between plants, leading to greater proportion of deaths of "thief-tillers" because they require energy from the plant and do not directly respond in yield.

Example 3: Interaction of Alginate with Micronutrients Such as Zn, Mo, Zn+Mo in the Treatment of Setts of Sugarcane Interaction of micronutrients with alginate for the treatment of setts provided gain related to sprouting, tillering and shoot growth of the sugarcane, as shown in Table 7. The best blends of micronutrients with the alginate are shown to be: (B) Alginate+Zn (95+5% w/w); (D) Alginate+Mo (99+1% w/w); (F) Alginate+Zn+Mo (89+10+1% w/w); and (H) Alginate+Zn+Mo (99+0.5+0.5% w/w).

Table 7 provides average number of tillers per experimental unit (4 setts) and sugarcane shoot length due to the treatment of sugarcane setts (11 cm) with blends of alginate and micronutrients. Variety RB 86 7515, Uberlândia—MG, 2014.

TABLE 7

| Treatments to | Tillers/4 setts | | | Shoot length (cm) |
|---|---|---|---|---|
| 11 cm-setts | 15 DAP | 30 DAP | 52 DAP | 30 DAP |
| A-Blend Alginate Zn + Mo (10 + 0) | 2.2 | 2.6 | 2.6 | 47.0 |
| B-Blend Alginate Zn + Mo (5 + 0) | 3.0 | 3.4 | 3.4 | 45.0 |
| C-Blend Alginate Zn + Mo (0 + 5) | 3.0 | 3.0 | 2.8 | 30.4 |
| D-Blend Alginate Zn + Mo (0 + 1) | 3.2 | 3.4 | 3.4 | 34.2 |
| E-Blend Alginate Zn + Mo (0 + 0.5) | 2.0 | 2.8 | 2.8 | 35.8 |
| F-Blend Alginate Zn + Mo (10 + 1) | 3.0 | 3.6 | 3.6 | 42.4 |
| G-Blend Alginate Zn + Mo (5 + 0.5) | 2.8 | 3.0 | 2.8 | 31.4 |
| H-Blend Alginate Zn + Mo (0.5 + 0.5) | 3.4 | 3.4 | 3.4 | 44.8 |
| Control without Alginate | 2.6 | 2.6 | 2.4 | 36.2 |
| Control with Alginate | 2.8 | 3.4 | 3.4 | 37.8 |

Example 4: Increased the Planting Yield by the Use of Small Setts Treated with Alginate As shown below, Table 8 provides the comparisons between sugarcane planting yield using small setts under two different cut regulations and large standard setts. Those of ordinary skill in the art can appreciate that the instant process steps provide much higher operational yields as compared to currently practiced methodologies.

TABLE 8

| Treatment | Weight/ hectare | sett weight (kg) | setts/ hectare | % setts with Buds | setts with buds/hectare | % buds Damage | setts with good | buds/ sett | Buds/ hectare | Hectares Planted | % related to the standard |
|---|---|---|---|---|---|---|---|---|---|---|---|
| Small Sett Harvester Regulation 1 | 90000 | 0.074 | 1216216 | 48 | 583784 | 18.4 | 476368 | 1.0 | 476368 | 5.95 | −25.0 |
| Large Sett | 90000 | 0.205 | 439024 | 83.7 | 367463 | 6.6 | 343211 | 1.9 | 634940 | 7.94 | 0 |
| Small Sett Harvester Regulation 2 | 90000 | 0.072 | 1250000 | 70 | 875000 | 13.5 | 756875 | 1.0 | 756875 | 9.46 | 19.2 |

Figure 11A:
FIG. 11: A. is a picture illustrating the coverage area of by the leaf canopy in a plot planted with Large standard setts 120 days after planting. B. is the same picture in Image J software to better quantify the leaf surface.
Figure 11B:
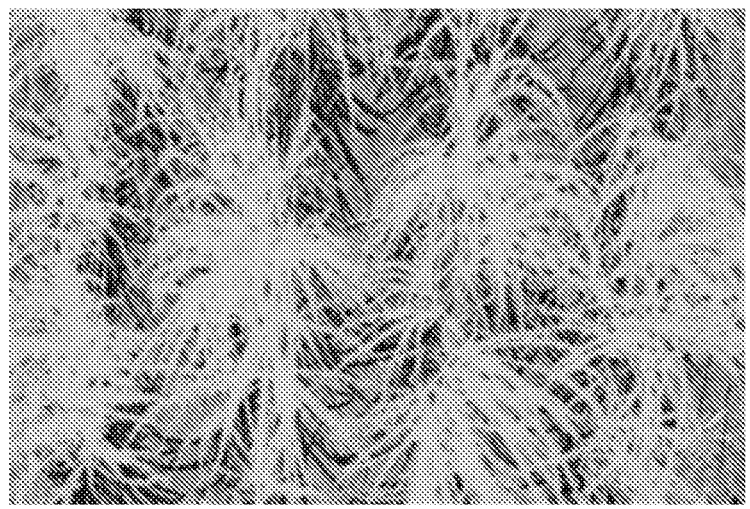
Figure 12A:
FIG. 12: A. is a picture illustrating the coverage area of by the leaf canopy in a plot planted with small setts treated with alginate 120 days after planting. B. is the same picture in Image J software to better quantify the leaf surface.
Figure 12B:
Figure 13A:
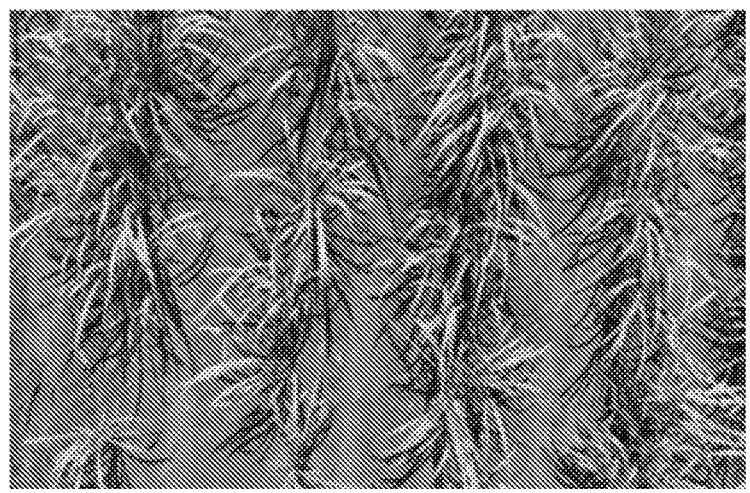
FIG. 13: A. is a picture illustrating the coverage area of by the leaf canopy in a plot planted with untreated small setts 120 days after planting. B. is the same picture in Image J software to better quantify the leaf surface.
Figure 13B:
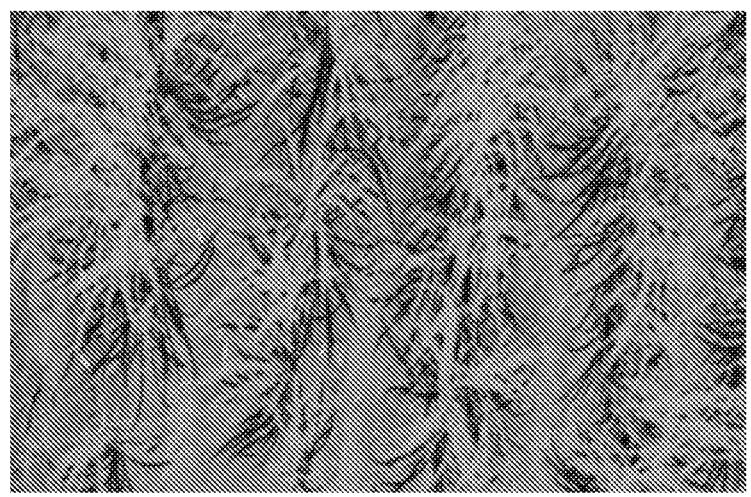
Figure 14:
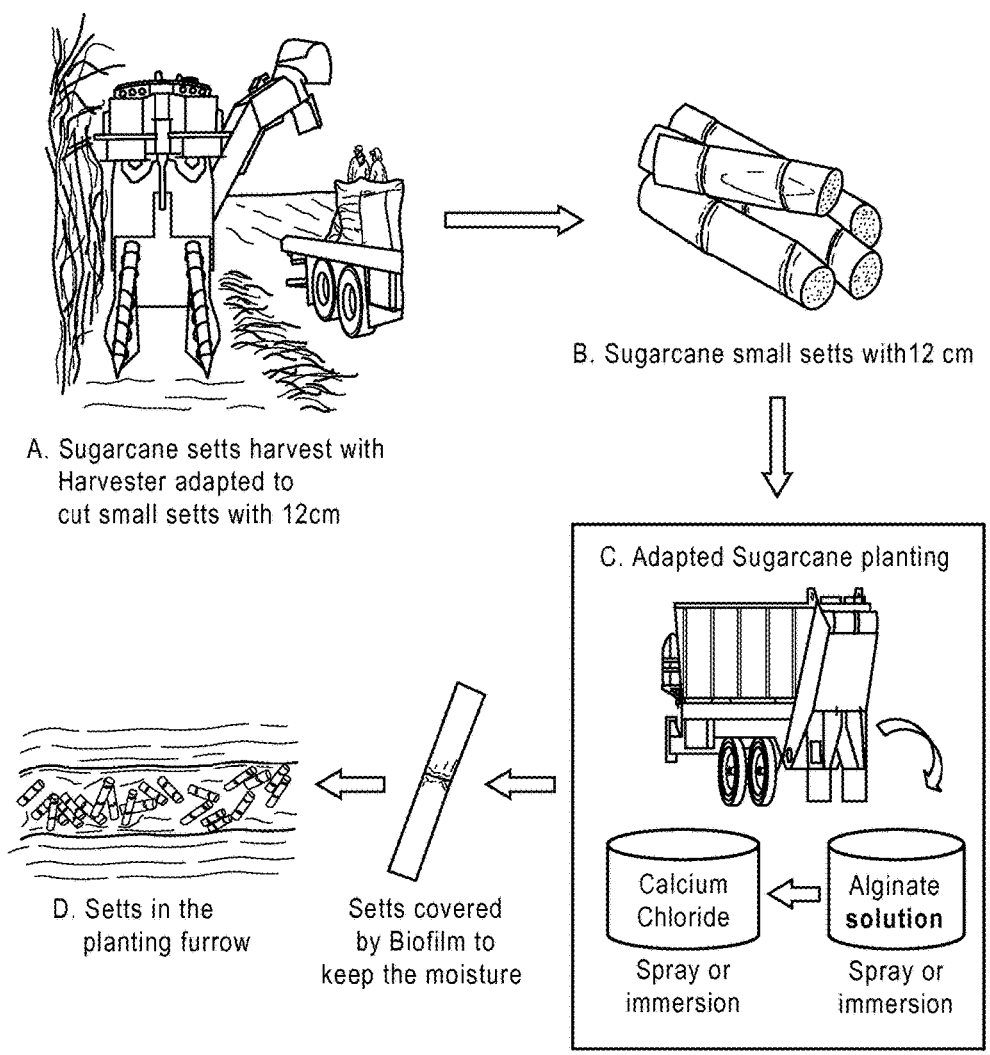
FIG. 14. Provides the sequence of the steps according to the present system. In step A, the system provides for a platform where sugarcane setts are processed through a harvester adapted to cut setts to sufficient sizes. In step B the exemplified sett are depicted. In step C, the sugarcane setts are adapted for planting and covered by the suitable biofilm. In step D the treated setts are planted in furrow.

In at least one example, the technology used to treat the small setts resulted in an operational gain 19.2% higher vs. the lager setts, as shown in Table 8. This outcome means that one hectare yielding 90 tons of sugarcane is enough to plant 9.46 hectares using the small setts technology. For the larger setts, the same area produces planting material for 7.94 hectares. The crop development using these two different technologies were compared considering the canopy development via aerial pictures. Plots planted with large setts resulted in 83% of coverage (FIG. 11), while the plots with small setts treated with alginate resulted in 76% (FIG. 12). However, plots with untreated small setts showed only 46% of canopy coverage (FIG. 13). As such those of ordinary skill in the art would appreciate the great impact of the present technology in improving the yield.

Although the present invention has been described in considerable detail with reference to certain preferred embodiments thereof, other versions are possible. Therefore the spirit and scope of the invention should not be limited to the description and the preferred versions contained within this specification.

What is claimed is:

1. A method of sett treatment comprising:
   (a) pretreating setts with one or more crop protection agents selected from the group consisting of a fungicide, insecticide, nematicide or growth promoter;
   (b) applying to setts a coating of an alginate selected from the group consisting of sodium alginate and potassium alginate, optionally containing one or more nutrients; and
   (c) applying to setts a coating of a solution of a divalent metal ion selected from the group consisting of $Ca^{+2}$, $Ba^{+2}$ and $Zn^{+2}$, thereby crosslinking the alginate with the divalent metal ion.

2. The method of claim 1, wherein said divalent metal ion solution comprises an aqueous solution of a divalent metal salt.

3. The method of claim 2, wherein said divalent metal salt is a calcium salt.

4. The method of claim 3, wherein said calcium salt is selected from the group consisting of calcium chloride, calcium carbonate and calcium sulfate.

5. The method of claim 1, wherein said divalent metal ion solution is applied by spraying.

6. The method of claim 1, wherein the application of the alginate coating is via spraying.

7. The method of claim 1, wherein the crop protection agent is selected from the group consisting of imidacloprid and bifenthrin, carbofuran, and bifenthrin.

8. The method of claim 1, wherein the nutrients are micronutrients.

9. The method of claim 8, wherein the micronutrients are selected from the group consisting of Zn, Mo, and a combination thereof.

10. A composition comprising a sugarcane sett coated with a layer of a calcium alginate hydrocolloid.

11. The composition of claim 10, wherein the sett was pretreated with a fungicide, insecticide, nematicide, or growth promoter before coating with the alginate.

12. The composition of claim 10, wherein the sett was pretreated with an insecticide before coating with the alginate.

13. The composition of claim 10, wherein the insecticide is selected from the group consisting of imidacloprid plus bifenthrin, carbofuran, carbosulfan, bifenthrin plus carbosulfan, and bifenthrin.

14. The composition of claim 13, wherein the insecticide is selected from the group consisting of imidacloprid plus bifenthrin, carbofuran, and bifenthrin.

15. The composition of claim 10, wherein the insecticide comprises imidacloprid plus bifenthrin.

16. A system for improving the operational yield in sugarcane crop comprising the steps of
   (a) harvesting sugarcane crops, (b) employing a harvester to produce suitable sized setts, (c) treating said setts with an alginate composition comprising an alginate salt solution and a calcium salt solution wherein a crop protection compound comprising a fungicide, insecticide, nematicide, or growth promoter is applied prior to applying the alginate composition, and (d) depositing the treated setts in furrow.

17. The system of claim 16, wherein the suitable sized setts have at least one bud.

18. The system of claim 16, wherein the alginate composition forms a film at the distal portion of said suitable sized setts.

19. The system of claim 16, wherein said alginate salt solution is selected from the group consisting of sodium alginate and potassium alginate.

20. The system of claim 16, wherein said calcium salt is selected from the group consisting of calcium chloride, calcium carbonate and calcium sulfate.

21. The system of claim 19, wherein the concentration of said alginate salt solution is about 0.05% to about 20% of alginate salt in water.

22. The system of claim 21, wherein the suitable sized setts are in the ranges of 7.5 cm to 45 cm in length.

23. The system of claim 22, wherein the suitable sized setts are in the ranges of 10 cm to 15 cm in length.

24. The system of claim 16 wherein the crop protection compound is an insecticide.

25. The system of claim 24 wherein the insecticide comprises imidacloprid plus bifenthrin, carbofuran, carbosulfan, bifenthrin plus carbosulfan, or bifenthrin.

26. The system of claim 24, wherein the insecticide comprises imidacloprid plus bifenthrin, carbofuran, or bifenthrin.

27. The system of claim 24, wherein the insecticide comprises imidacloprid plus bifenthrin.

* * * * *